(12) United States Patent
Kawazoe

(10) Patent No.: US 6,681,783 B2
(45) Date of Patent: Jan. 27, 2004

(54) METHOD AND APPARATUS FOR CLEANING THE INTERIOR OF A CHANNEL OF A MEDICAL INSTRUMENT

(75) Inventor: Kaoru Kawazoe, 396-31, Urago, Togitsu-cho, Nishisonogi-gun, Nagasaki-ken (JP)

(73) Assignees: Kaoru Kawazoe, Nagasaki-ken (JP); Masahide Koga, Fukuoka-ken (JP)

( * ) Notice: Subject to any disclaimer, the term of this patent is extended or adjusted under 35 U.S.C. 154(b) by 50 days.

(21) Appl. No.: 09/973,942

(22) Filed: Oct. 11, 2001

(65) Prior Publication Data

US 2002/0069893 A1 Jun. 13, 2002

(30) Foreign Application Priority Data

Oct. 12, 2000 (JP) ........................................ 2000-312379

(51) Int. Cl.[7] .................................................. B08B 3/10
(52) U.S. Cl. .............................. 134/169 C; 134/167 C; 134/184
(58) Field of Search .................. 134/1, 184, 166 C, 134/169 C, 167 C, 168 C

(56) References Cited

U.S. PATENT DOCUMENTS

| | | | | |
|---|---|---|---|---|
| 2,437,456 A | * | 3/1948 | Bodine, Jr. | |
| 2,917,762 A | * | 12/1959 | Xenis | |
| 3,409,031 A | * | 11/1968 | Benbow et al. | |
| 3,421,939 A | * | 1/1969 | Jacke | |
| 3,427,480 A | * | 2/1969 | Robinson | |
| 3,446,666 A | * | 5/1969 | Bodine | |
| 3,946,459 A | * | 3/1976 | Armstrong | |
| RE30,536 E | * | 3/1981 | Perdreaux et al. | |
| 4,920,954 A | * | 5/1990 | Alliger et al. | |
| 5,240,675 A | * | 8/1993 | Wilk et al. | |
| 5,735,811 A | * | 4/1998 | Brisken | |
| 5,830,127 A | | 11/1998 | DeCastro | |
| 6,047,431 A | | 4/2000 | Canonica | |
| 6,221,038 B1 | * | 4/2001 | Brisken | |
| 6,474,349 B1 | * | 11/2002 | Laker | |

FOREIGN PATENT DOCUMENTS

| | | | |
|---|---|---|---|
| DE | 4432683 | * | 3/1996 |
| JP | 8-66668 | * | 3/1996 |
| WO | WO 99/44512 | | 9/1999 |
| WO | WO 00/30554 | | 6/2000 |

OTHER PUBLICATIONS

European Patent Office Search Report for the European application corresponding to the instant application.

* cited by examiner

Primary Examiner—Frankie L. Stinson
(74) Attorney, Agent, or Firm—Rothwell, Figg, Ernst & Manbeck

(57) ABSTRACT

A cleaning apparatus (1) for cleaning the interior surface of a channel of a medical instrument includes an ultrasonic cleaning device having a cleaning catheter (2) provided with ultrasonic vibrators (4, 5) for separating undesired matter from the interior surface of the channel (12) of the medical instrument by ultrasonic vibration; and an ultrasonic oscillator (8) for operating the ultrasonic vibrators (4, 5). The cleaning apparatus (1) further includes a cleaning liquid discharge device (13) having a cleaning liquid feeding tube (10) into which the cleaning catheter can be inserted with the ultrasonic vibrators (4, 5) exposed and which expels a cleaning liquid from a front end thereof; a cleaning liquid storing tank (14); and a pump (16) for feeding the cleaning liquid.

7 Claims, 7 Drawing Sheets

METHOD AND APPARATUS FOR CLEANING THE INTERIOR OF A CHANNEL OF A MEDICAL INSTRUMENT

BACKGROUND OF THE INVENTION

The present invention relates to a method and an apparatus for cleaning the inside of a narrow channel or channel of a medical instrument such as an endoscope, a surgical instrument, and the like. More particularly, the present invention relates to a method and an apparatus for reliably removing materials such as mucus, blood, and the like which have adhered to the inner surface of the channel.

The use of endoscopes has spread rapidly and widely in the medical field, and endoscopic operations are performed frequently. However, with the increasing number of endoscopic examinations being performed in recent years, infections are on the rise. Insufficiently cleaned endoscopes cause most of these infections.

A large number of medical instruments for use in conjunction with endoscopes have been developed. Many of these medical instruments have complicated configurations, such as coil-shaped long, narrow tubes, that are difficult to clean. Infections due to insufficient cleaning of these instruments are on the rise and have become a significant problem. Thus, there is a great demand for the development of methods of preventing infections from occurring at the time of examination and treatment.

The preparatory step in cleaning the endoscope involves removal of mucus and blood (materials composed of mainly protein and fatty components) with a diluted solution of detergent containing an enzyme that decomposes fat and protein. This preparatory cleaning step should be performed before performing the subsequent operation of sterilizing the endoscope.

There are many imperfections on the inner surfaces of the channels of endoscopes through which bioptic and/or other instruments pass. Organic matter may adhere to these flaws, leading to the growth of bacteria and subsequent infection of patients. Additionally, such contaminants adhere to the inner surfaces of suction channels. Further, there is a possibility that bacteria will penetrate into a cavity or imperfection at the location where tubes or channels are interconnected, or on the inner surface of such tubes. Thus, it has become accepted and viewed as essential to clean the interiors of the various channels of the medical instrument with a cleaning brush.

Current practice involves manually cleaning channels of medical instruments such as endoscopes with a cleaning brush that is exclusively used for that purpose, while allowing water to flow into the channels (e.g., the clamp channel and the suction channel). Repeated brushing/scrubbing operations are necessary. Unfortunately it is possible for the tip of the cleaning brush to rub contaminants into the inner surface of the clamp channel and the suction channel after it is separated from the cleaning brush. Furthermore, it is difficult for running water to flow smoothly through the channels. As a result, the water cannot carry away the contaminants. In addition, the tip of the cleaning brush can damage the inner surface of the clamp channel and the suction channel to form cavities or irregularities, whereby bacteria or viruses can enter the cavities and become entrapped. This is also a problem. Commercially available cleaning brushes are much larger than bacteria and viruses. Thus, it is impossible for the cleaning brush to remove pathogenic bacteria which have entered into a fine flaw or cavity inside the channel.

Many cleaning devices for cleaning medical instruments, such as endoscopes, by using ultrasonic waves have been proposed. However, these cleaning devices are used to clean the outer surface of the medical appliance and cannot clean the internal, narrow channels.

The high cost of endoscopes precludes hospitals and other medical establishments from having many of them. Accordingly, to use the endoscope safely and efficiently, there is a demand for the development of a method and an apparatus capable of accomplishing effective cleaning of the inside of a channel of an endoscope or other medical instrument in a relatively short period of time.

There is a limitation in the method of injecting chemicals commercially available into each channel of the endoscope and manually brushing the inner surface of each channel with a cleaning brush. As a result, after an incomplete cleaning is performed, a non-sterile endoscope may be used on patients.

SUMMARY OF THE INVENTION

The present invention provides a method and an apparatus capable of easily and reliably cleaning the inside of a channel of a medical appliance (instrument) such an endoscope.

In one aspect, the invention provides a method for cleaning the inside of a channel of a medical instrument comprising the steps of:
   inserting a cleaning catheter having an ultrasonic vibrator mounted thereon into a channel of said medical instrument; and
   vibrating said ultrasonic vibrator and moving said cleaning catheter in said channel to transmit an ultrasonic vibration to an inner surface of said channel, whereby said ultrasonic vibration induces undesirable matter disposed the inner surface of said channel to separate from said inner surface.

In another aspect, the invention provides a cleaning apparatus for cleaning an inside of a channel of a medical instrument, comprising:
   a cleaning catheter that comprises an ultrasonic vibrator that can be inserted into said channel; and
   an ultrasonic oscillator for operating said ultrasonic vibrator.

In yet another aspect, the invention provides a method for cleaning an interior surface of a channel of a medical instrument, comprising the steps of:
   inserting into said channel a cleaning catheter comprising an ultrasonic vibrator, with a cleaning liquid-feeding tube surrounding said cleaning catheter, said ultrasonic vibrator being exposed into said channel of said medical instrument;
   expelling cleaning liquid from a gap between said cleaning catheter and said cleaning liquid-feeding tube; and
   operating said ultrasonic vibrator to cause ultrasonic vibrations to impinge upon the inside of said channel, whereby undesirable matter is separated from an inner surface of said channel by said ultrasonic vibrations and transported through said channel by said cleaning liquid.

In another aspect, the invention provides a cleaning apparatus for cleaning the interior of a channel of a medical instrument, comprising:
   an ultrasonic cleaning device comprising a cleaning catheter including an ultrasonic vibrator;
   an ultrasonic oscillator for operating said ultrasonic vibrator; and a cleaning liquid discharge device comprising a cleaning liquid-feeding tube into which said cleaning catheter can be inserted with said ultrasonic vibrator exposed, a cleaning liquid discharge port, a cleaning liquid storage tank and a pump for feeding cleaning liquid from said tank to said discharge port.

DETAILED DESCRIPTION OF THE PREFERRED EMBODIMENTS

Figure 1:
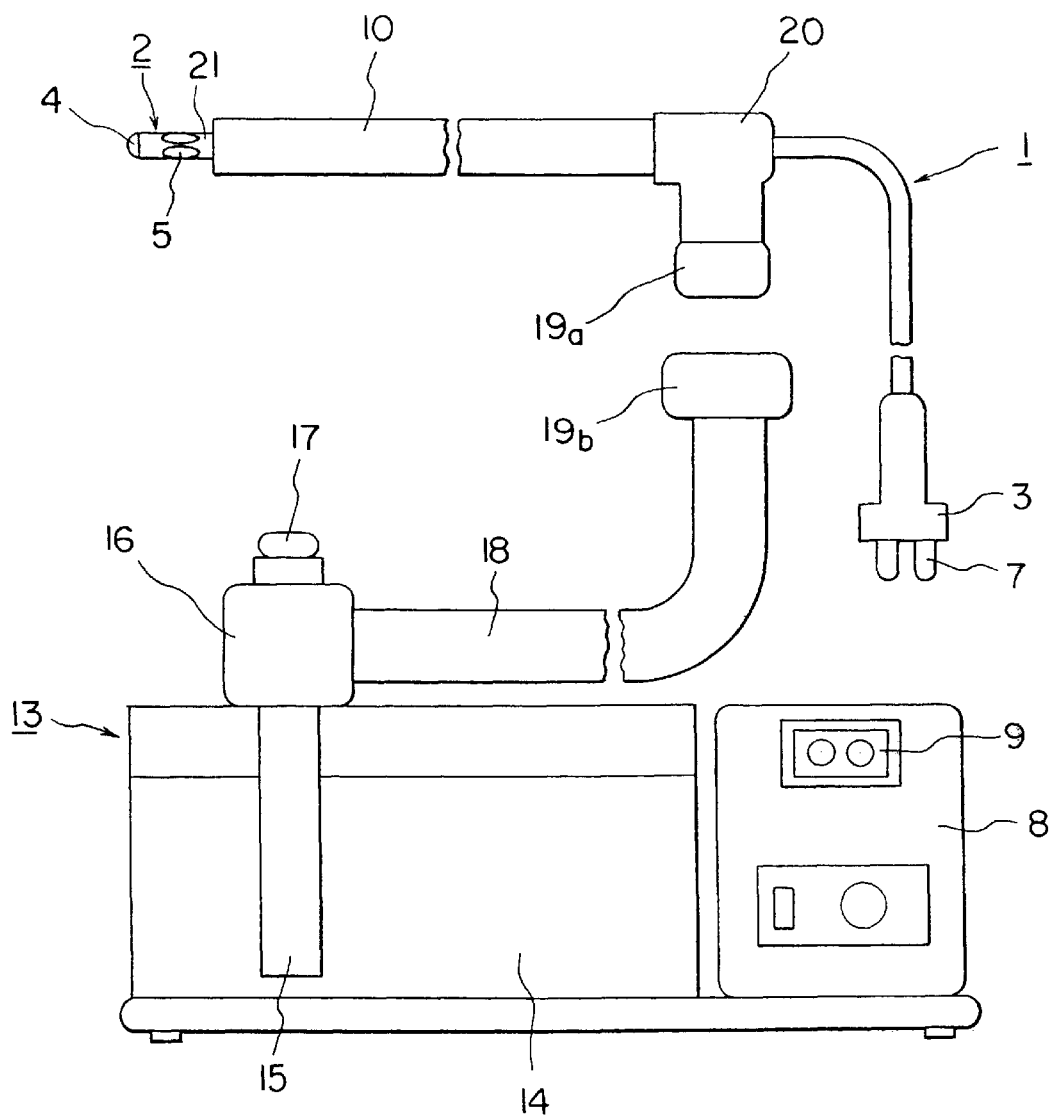
FIG. 1 is a schematic construction view showing a cleaning apparatus according to an embodiment of the present invention, for cleaning the inside of a channel of a medical instrument.

The method and the apparatus for cleaning the inside of a channel of a medical instrument according to preferred embodiments of the present invention will be described in detail below with reference to the drawings.

The method of the present invention for cleaning the inside of the channel of a medical instrument includes the steps of inserting a cleaning catheter 2 having ultrasonic vibrators 4, 5 mounted thereon into a channel 12 of the medical instrument, of vibrating the ultrasonic vibrators 4, 5 and moving the cleaning catheter 2 in the channel 12 to transmit an ultrasonic vibration to an inner surface of the channel 12 and separate (remove) undesired matter from the inner surface of the channel 12.

It is possible to transmit the ultrasonic vibration emitted from the cleaning catheter 2 to the entire inner surface of the channel 12 of the medical instrument by inserting the cleaning catheter 2 into the channel 12 and moving it in the channel 12, namely, by moving the cleaning catheter forward and rearward in the axial direction of the channel. Thereby, the undesired matter (or in other words, a contaminant), which has adhered to the inner surface of the channel of the medical instrument, is subjected to the ultrasonic vibration and separates therefrom while it is being pulverized. The inner surface of the channel of the medical instrument is cleaned with a cleaning liquid such as cleaning water or a diluted solution containing cleaning chemicals supplied (expelled) into the channel.

A cleaning apparatus 1 of the present invention for cleaning the inside of the channel 12 of the medical instrument includes the cleaning catheter 2 which has ultrasonic vibrators 4, 5 for separating undesired matter from the matter-adhered inner surface of the channel 12 of the medical instrument by means of the ultrasonic vibration and which can be inserted into the channel 12; and an ultrasonic oscillator 8 for operating the ultrasonic vibrators 4, 5.

The ultrasonic vibration can be transmitted to the entire inner surface of the channel 12, and the adhered contaminant can be separated therefrom by inserting the cleaning catheter 2 of the cleaning apparatus 1 into the channel 12 of the medical instrument and moving the cleaning catheter 2 in the channel while the ultrasonic vibrators 4, 5 are being vibrated successively or intermittently by using the ultrasonic oscillator 8. The separated matter is removed from the channel by supplying the cleaning liquid such as cleaning water or the diluted solution containing cleaning chemicals into the channel 12 so that the cleaning liquid can flow through the channel and carry with it the undesirable matter.

Figure 2:
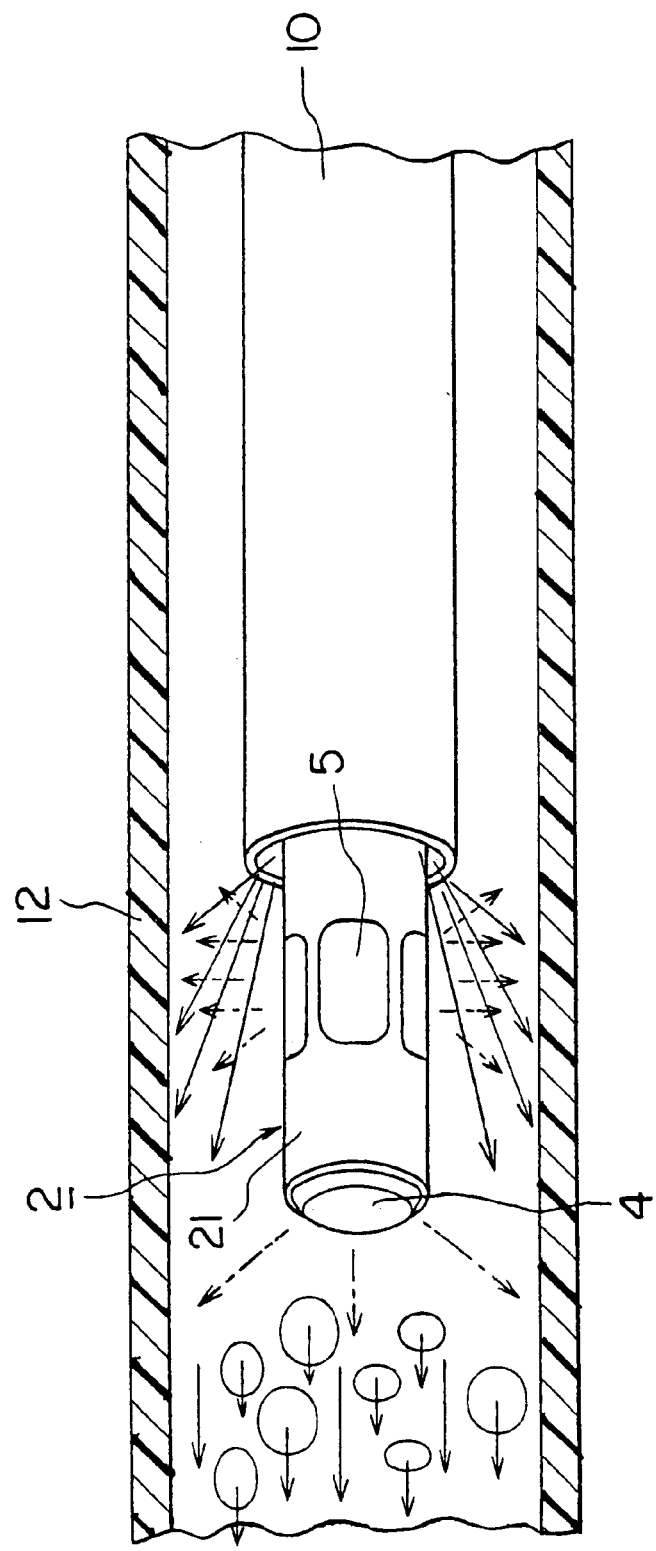
FIG. 2 is an explanatory view showing the use of the cleaning apparatus shown in FIG. 1.

In the cleaning apparatus 1 shown in FIG. 2, because the ultrasonic vibrator 4 is mounted at the front end of the cleaning catheter 2, the ultrasonic vibration can be transmitted forward in a wide range of the cleaning catheter 2.

In the cleaning apparatus 1 shown in FIG. 2, a plurality of ultrasonic vibrators 5 are installed on the peripheral surface of the cleaning catheter 2. Thus, the ultrasonic vibration can be imparted to the inner surface of the channel from a position close to the inner surface of the channel and almost perpendicularly to the inner surface of the channel. Therefore, the ultrasonic vibration can be efficiently imparted to the matter that has adhered to the inner surface of the channel, and the contaminant can be reliably separated (removed) from the inner surface of the channel of the medical instrument.

In the cleaning apparatus 1 shown in FIG. 2, the ultrasonic vibrator is mounted on both the front end and peripheral surface of the cleaning catheter 2. Thus, with the movement of the cleaning catheter 2 in the channel 12, it is possible to impart the ultrasonic vibration to the inner surface of the channel 12 at different angles from the ultrasonic vibrator 4 mounted on the front end of the cleaning catheter 2 and the ultrasonic vibrator 5 mounted on the peripheral surface thereof. That is, the ultrasonic vibration can be uniformly transmitted to the inside of the channel 12. Therefore, the contaminant can be reliably separated from the inner surface of the channel.

The method of the present invention for cleaning the inside of the channel of the medical instrument has the step of inserting the cleaning catheter 2 having the ultrasonic vibrators 4, 5 mounted thereon and the cleaning liquid-feeding tube 10, for expelling the cleaning liquid, provided in such a way as to surround the cleaning catheter 2 with the ultrasonic vibrator exposed into the channel 12 of the medical instrument and the step of expelling the cleaning liquid from the gap between the cleaning catheter 2 and the cleaning liquid-feeding tube 10 and operating the ultrasonic vibrators 4, 5 to separate the matter from the matter-adhered inner surface of the channel 12 of the medical instrument by an ultrasonic vibration and carry the separated matter forward by the cleaning liquid.

According to the cleaning method, the matter that has adhered to the inner surface of the channel 12 of the medical instrument is separated from the surface the ultrasonic wave emitted from the ultrasonic vibrators 4, 5 mounted on the cleaning catheter 2. The expelled cleaning liquid carries the separated matter forward. Further, the ultrasonic wave emitted from the ultrasonic vibrators 4, 5 mounted on the cleaning catheter 2 deteriorates the adhesive force of the matter that has adhered to the inner surface of the channel 12 of the medical instrument. Consequently, the jetted cleaning liquid separates the matter from the inner surface of the channel 12 and carries it forward.

The cleaning apparatus 1 of the present invention includes an ultrasonic wave cleaning device having the cleaning catheter 2 provided with the ultrasonic vibrators 4, 5 for separating the matter from the matter-adhered inner surface of the channel 12 of the medical instrument by the ultrasonic vibration and the ultrasonic oscillator 8 for operating the ultrasonic vibrators 4, 5; and a cleaning liquid discharge device 13 including the cleaning liquid-feeding tube 10 into which the cleaning catheter 2 can be inserted with the ultrasonic vibrator exposed and which jets the cleaning liquid from the front end thereof, a cleaning liquid-storing tank 14, and a pump 16 for feeding the cleaning liquid at a high pressure to the cleaning liquid-feeding tube 10. The cleaning liquid-feeding tube 10 of the cleaning liquid discharge device 13 jets the cleaning liquid from its front end.

Figure 5:
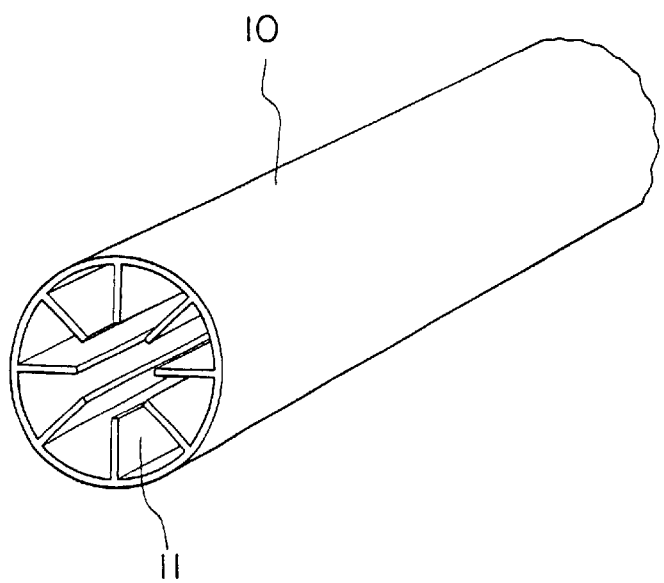
FIG. 5 is a perspective view showing a front side of another example of a cleaning liquid feeding tube of the cleaning apparatus as of the present invention.

As shown in FIG. 5, showing another embodiment, the cleaning liquid-feeding tube 10 may be provided with a plurality of ribs (in other words, a partitioning wall) 11 extending from the inner peripheral surface thereof toward its center to make the interval between the cleaning liquid-feeding tube 10 and the cleaning catheter 2 almost uniform circumferentially. The rib 11 allows the cleaning liquid having a high pressure to be jetted uniformly and radially to the peripheral surface of the front side of the cleaning catheter 2 and allows the inner surface of the channel of the medical instrument to be washed reliably and uniformly.

The method and apparatus of the present invention for cleaning the inside of the channel of the medical instrument will be described below by exemplifying a cleaning apparatus for cleaning the inside of a suction channel of an endoscope, which is the largest source of infection in examination.

As shown in FIGS. 1 through 6, a cleaning apparatus 1 for cleaning the inside of a suction channel of an endoscope includes the cleaning catheter 2 which is an ultrasonic wave-cleaning probe and the ultrasonic oscillator 8.

Figure 6:
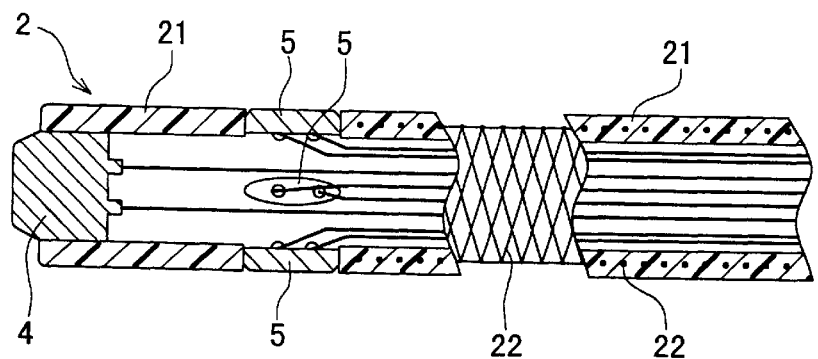
FIG. 6 is an enlarged sectional view showing a front part of another example of a cleaning catheter of the cleaning apparatus of the present invention.

As shown in FIG. 2 and FIG. 6, which is an enlarged sectional view showing the front side of the cleaning catheter 2, the cleaning catheter 2 includes a large-diameter vibrator 4 sealing the front end of a catheter tube 21; a plurality of small vibrators 5 provided on the peripheral surface of the front side of the catheter tube 21; and a connector 3 connecting the cleaning catheter 2 and the ultrasonic oscillator 8 provided on the rear end of the catheter tube 21 to each other. In the case where a plurality of the small vibrators 5 are mounted on the peripheral surface of the front side of the catheter tube 21, it is preferable to arrange the small vibrators 5 annularly in such a way that they form equal central angles in the circumference of the axis of the catheter tube 21. It is favorable to mount from two to eight small vibrators 5 on the peripheral surface of the front side of the catheter tube 21 and more favorable to mount from three to six small vibrators 5 thereon.

A flexible tube is used as the body (catheter tube) of the cleaning catheter. The length of the catheter tube is favorably 50–200 cm and more favorably 150–200 cm. The outer diameter of the catheter tube is favorably 1–5 mm and more favorably 1.8–2.6 mm.

As the material for the catheter tube 21, the following thermoplastic resins are preferable: olefin resins such as polyethylene, polypropylene, polybutylene, ethylene-vinyl acetate copolymer or polyolefin elastomers thereof, fluorocarbon resin or soft fluorocarbon resin, methacrylate resin, polyphenylene oxide, modified polyphenylene ether, polyethylene terephthalate, polybutylene terephthalate, polyurethane elastomer, polyester elastomer, polyamide or polyamide elastomer, polycarbonate, polyacetal, styrene resin or styrene elastomer, and thermoplastic polyimide. It is possible to use a polymer alloy or a polymer blend containing any one or more of these resins as a base material thereof.

A rigidity-imparting member 22 may be mounted on the catheter tube 21 to prevent bending of the catheter tube 21 and increase the torque performance thereof. It is preferable to arrange the rigidity-imparting member 22 in the range from the rear end of the catheter tube 21 to the vicinity of the position at which the small vibrator (ultrasonic vibrator) 5 is installed.

It is preferable that the rigidity-imparting member 22 is reticulate. It is preferable that the reticulate rigidity-imparting member is made of braided wires. The rigidity-imparting member 22 can be formed of metal wires of stainless steel, elastic metal, ultra-high elastic alloy, or shape-storing alloy. The diameter of the metal wire is favorably in the range of 0.01–0.2 mm and more favorably in the range of 0.03–0.1 mm. The rigidity-imparting member may be formed of synthetic fibers such as polyamide fiber, polyester fiber, and polypropylene fiber.

It is possible to use the large-diameter vibrator (in other words, the vibrator to be installed at the front end of the catheter tube) 4 radiating an ultrasonic energy having a short wavelength of several hundreds of kilohertz to several megahertz or the large-diameter vibrator 4 radiating an ultrasonic energy having a relatively long wavelength of several tens of kilohertz. As the ultrasonic vibrator (large-diameter vibrator) 4, it is possible to use a piezoelectric ceramic vibrator, a metal magnetostrictive vibrator, or a ferrite magnetostrictive vibrator. It is preferable to use the piezoelectric ceramic vibrator. The piezoelectric ceramic vibrator made of PZT (lead zirconate titanate) is particularly preferable.

The vibrator 4 to be installed at the front end of the catheter tube has an outer diameter almost equal to the inner diameter of the opening formed at the front end of the catheter tube 21. The vibrator 4 is fitted in the opening formed at the front end of the catheter tube 21. An adhesive agent (not shown) is applied to the peripheral edge of the vibrator 4 and the inner peripheral edge of the opening formed at the front end of the catheter tube 21. Thus, the gap therebetween is liquid-tight.

It is possible to use the small vibrator (in other words, the vibrator to be installed on the peripheral surface of the catheter tube) 5 radiating an ultrasonic energy having a short wavelength of several hundreds of kilohertz to several megahertz or the large-diameter vibrator 4 radiating an ultrasonic energy having a relatively long wavelength of several tens of kilohertz. As the ultrasonic vibrator (small vibrator) 5, it is possible to use a piezoelectric ceramic vibrator, a metal magnetostrictive vibrator, or a ferrite magnetostrictive vibrator. It is preferable to use the piezoelectric ceramic vibrator. The piezoelectric ceramic vibrator made of PZT (lead zirconate titanate) is particularly preferable.

To use only one oscillation circuit, it is preferable that the vibrators 5 to be installed on the peripheral surface of the catheter tube oscillate ultrasonic waves having the same frequency. However, vibrator 5 and the vibrator 4 may oscillate ultrasonic waves having the same or different frequencies.

The vibrator 5 to be installed on the peripheral surface of the catheter tube 21 is located at a position spaced at a predetermined interval from the front end of the catheter tube 21. More specifically, the vibrator 5 is located at a position spaced at 1–10 mm and favorably 2–3 mm from the front end of the catheter tube 21. A plurality of side openings whose configurations match that of the vibrator 5 are formed at positions on the peripheral surface of the catheter tube where the vibrators 5 are disposed. An unshown adhesive agent is applied to the peripheral edge of each vibrator 5 and the inner peripheral edge of each side opening. Thus, the gap therebetween is liquid-tight.

Figure 3:
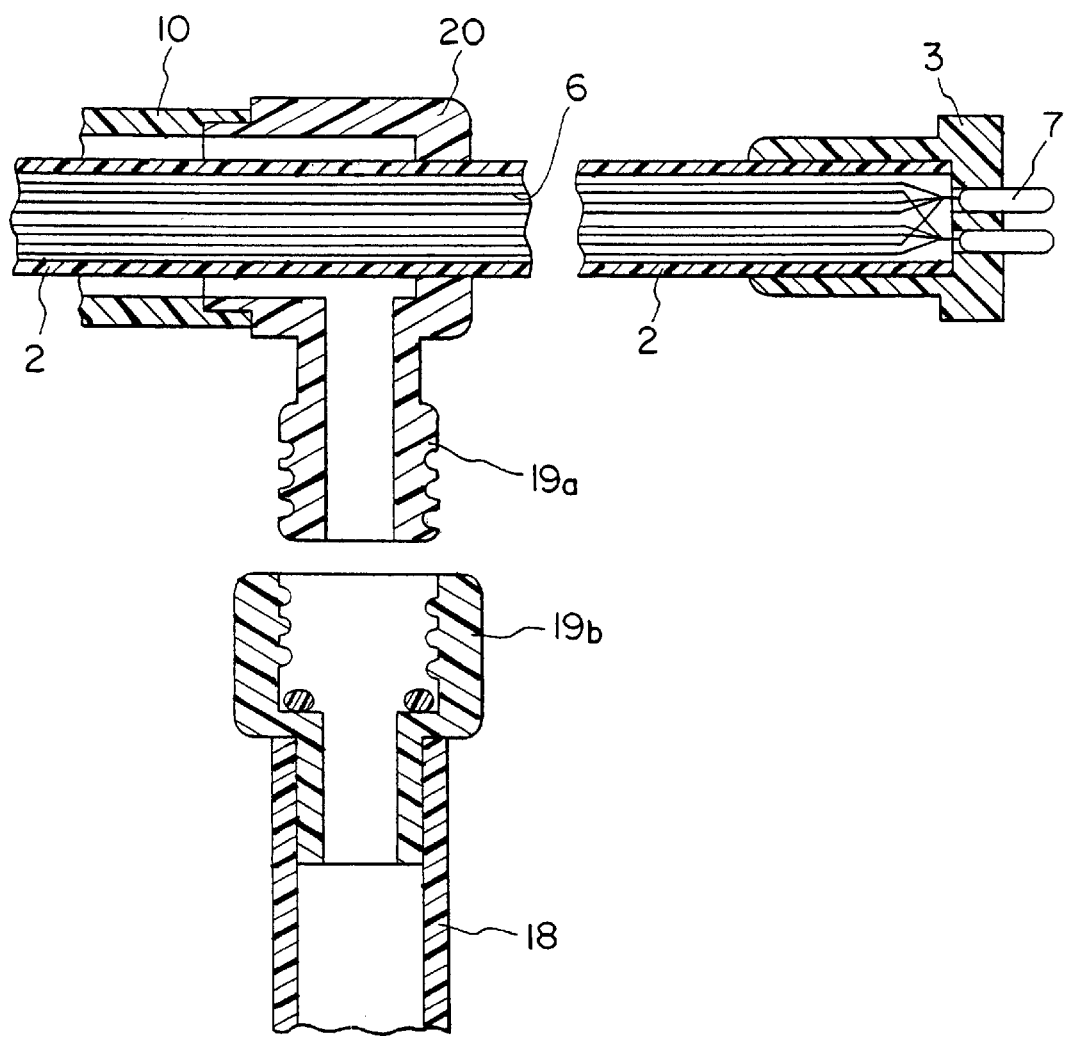
FIG. 3 is a partly broken-away sectional view showing the cleaning apparatus of the present invention at a part thereof in the vicinity of a rear end of a cleaning liquid feeding tube.
Figure 4:
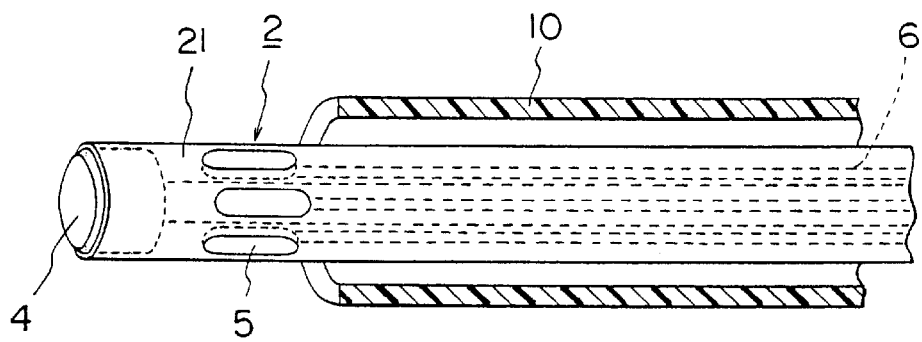
FIG. 4 is a partly broken-away sectional view showing the cleaning apparatus of the present invention at a part thereof in the vicinity of a front end of a cleaning catheter.

As shown in FIG. 3, two lead wires 6 are connected to each of the vibrators 4, 5. The lead wires 6 pass through the inside of the catheter tube and are connected to terminals 7 of the connector 3. All the lead wires 6 may be bundled to form one cord. The connector 3 has a shape and a construction so as to make it connectable to a connector connection portion 9 of the ultrasonic oscillator 8. By connecting the connector 3 to the ultrasonic oscillator 8, a wave motion emitted by the ultrasonic oscillator 8 is transmitted to the vibrators 4, 5 through the terminal 7 and the lead wire 6.

Figure 7:
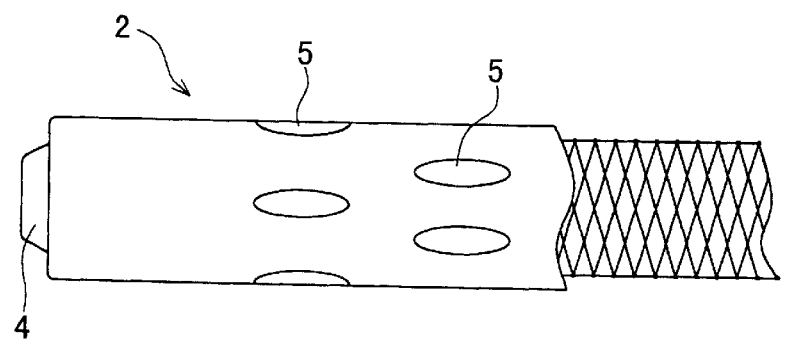
FIG. 7 is an enlarged front view showing a front part of still another example of a cleaning catheter of the cleaning apparatus of the present invention.
Figure 8:
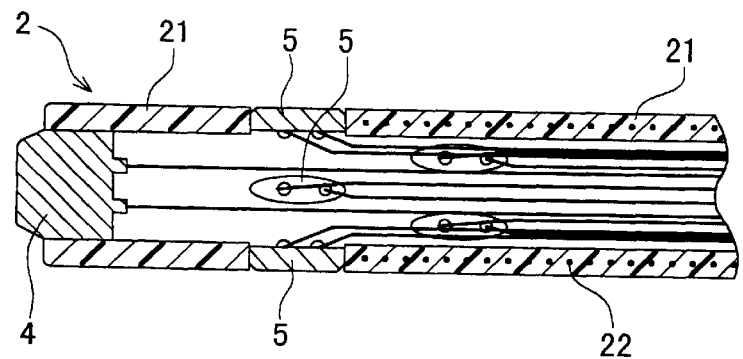
FIG. 8 is a sectional view showing the cleaning catheter shown in FIG. 7.

As shown in FIGS. 7 and 8 showing another embodiment, it is possible to annularly install a plurality of rows each consisting of a plurality of the vibrators 5 on the peripheral surface of the cleaning catheter 2.

FIG. 7 is an enlarged front view of the front side of the cleaning catheter 2 according to another embodiment of the present invention. FIG. 8 is a sectional view of the cleaning catheter shown in FIG. 7.

The cleaning catheter 2 of the embodiment has two rows of the vibrators 5 mounted on the peripheral surface thereof. But the cleaning catheter 2 may have three or more rows of the vibrators 5 mounted on the peripheral surface thereof. In the case where the cleaning catheter 2 has two rows of the vibrators annularly mounted on the peripheral surface thereof, it is prefer able that the vibrators 5 of a first row, namely, the vibrators 5 in a row at the front side of the cleaning catheter 2 are arranged at equal intervals in the circumference of the axis of the catheter tube 21. Similarly, it is preferable that the small vibrators of a second row, namely, the small vibrators 5 in a row at the rear side of the cleaning catheter 2 with respect to the first row are arranged at equal intervals in the circumference of the axis of the catheter tube 21. It is also preferable that when the catheter is viewed in its axial direction, each of the small vibrators 5 of the second row are disposed on an extension drawn axially between the adjacent small vibrators 5 of the first row. In the embodiment shown in FIGS. 7 and 8, four small vibrators 5 of the first row are arranged at equal intervals of 90 degrees in the circumference of the axis of the catheter tube 21. Four small vibrators 5 of the second row are also arranged at equal intervals of 90 degrees in the circumference of the axis of the catheter tube 21 in such a manner that they are displaced by 45 degrees with respect to the small vibrators 5 of the first row. Therefore, the small vibrator 5 of the second row is located on the extension drawn axially between the adjacent small vibrators 5 of the first row.

Figure 9:
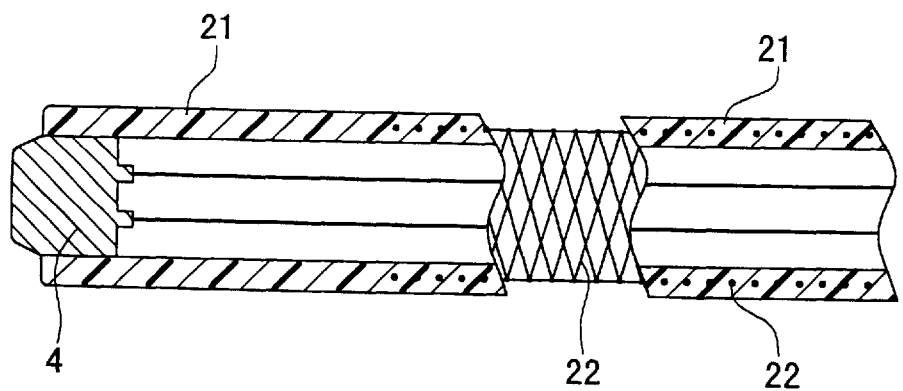
FIG. 9 is an enlarged sectional view showing a front part of still another example of a cleaning catheter of the cleaning apparatus of the present invention.

As shown in FIG. 9 showing another embodiment, the cleaning catheter 2 may have only the vibrator 4 at the front end thereof. That is, it is possible that the vibrator 5 is not mounted on the cleaning catheter 2.

Figure 10:
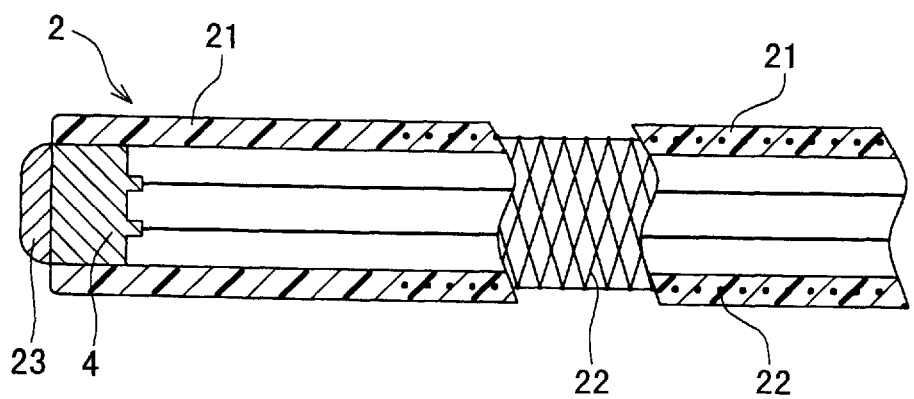
FIG. 10 is an enlarged sectional view showing a front part of still another example of a cleaning catheter of the cleaning apparatus of the present invention.
Figure 11:
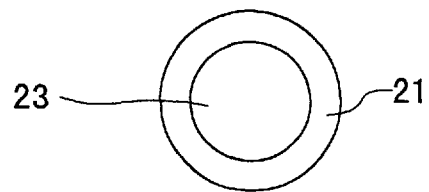
FIG. 11 shows a front end surface of the cleaning catheter shown in FIG. 10.

In the case where the cleaning catheter 2 is provided with only the vibrator 4 at the front end thereof, as shown in FIG. 10, an oscillation surface of the vibrator 4 may be provided with a vibration direction conversion member 23 for converting a longitudinal (axial direction of cleaning catheter) vibration into a radial (orthogonal to the axial direction of cleaning catheter) vibration. It is favorable for the vibration direction conversion member 23 to be disc-shaped or polygonal plate-shaped. The disc-shaped vibration direction conversion member 23 is more favorable than the polygonal plate-shaped one. FIG. 11 shows the front end surface of the cleaning catheter 2 shown in FIG. 10. The vibration direction conversion member 23 allows the ultrasonic wave to be reliably directed to the inner peripheral surface of the channel of the medical instrument. Also, in the case where the cleaning catheter 2 is provided with the vibrator 4 and the vibrator 5, an oscillation surface of the vibrator 4 may be provided with a vibration direction conversion member 23 for converting a longitudinal (axial direction of cleaning catheter) vibration into a radial (orthogonal to the axial direction of cleaning catheter) vibration.

The ultrasonic vibrators 4, 5 may be provided with an unshown vibration protection film. The vibration protection film is formed from an ultrasonic wave-transmittable material. Polyolefin resin, polyurethane resin, and fluorocarbon resin can be preferably used to compose the ultrasonic wave-transmittable material.

Figure 12:
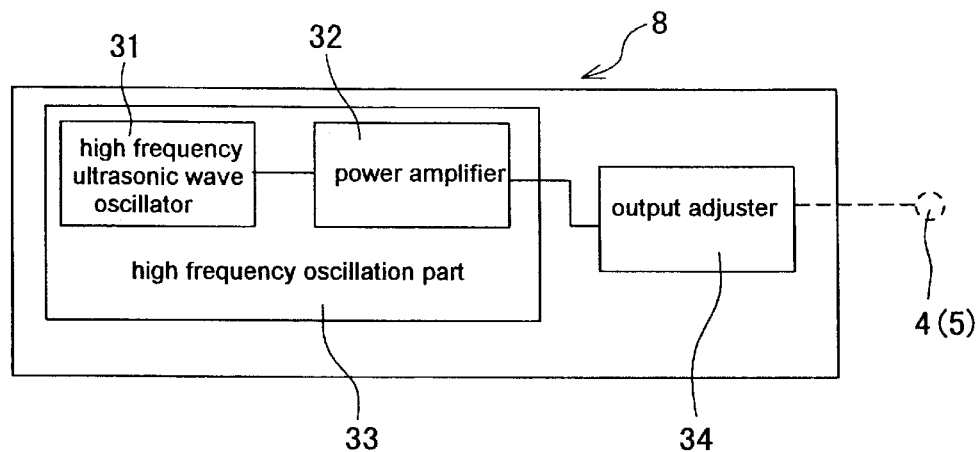
FIG. 12 is an explanatory view of an ultrasonic oscillator of the cleaning apparatus of the present invention.
Figure 13:
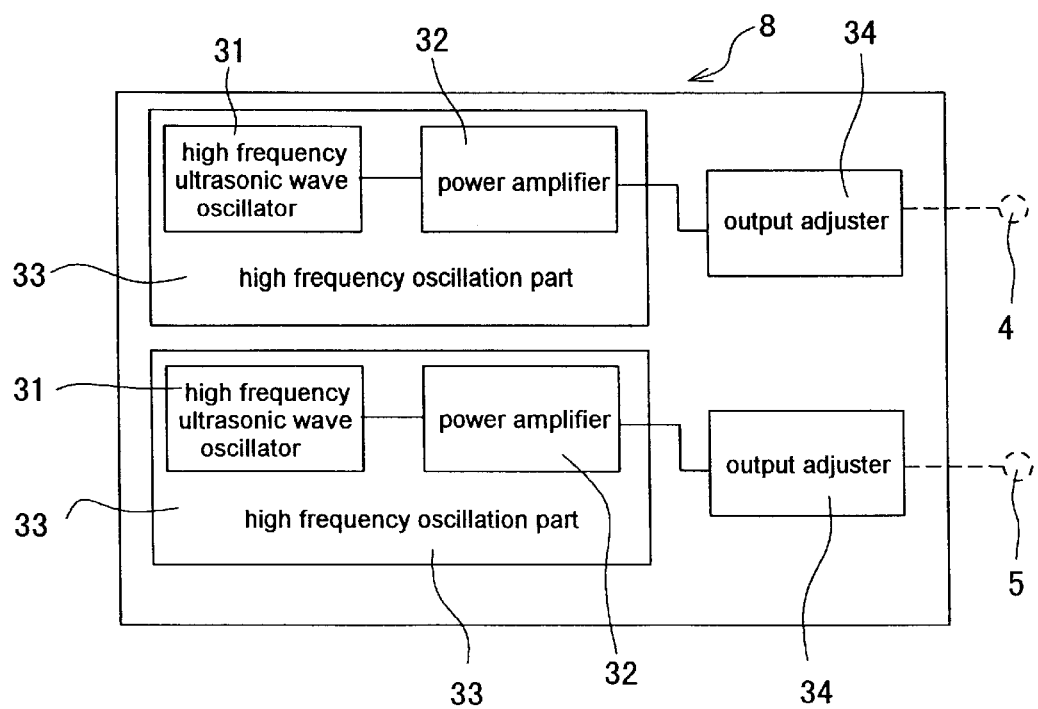
FIG. 13 is an explanatory view of another ultrasonic oscillator of the cleaning apparatus of the present invention.

The ultrasonic oscillator 8 is a device for oscillating the vibrator. As the ultrasonic oscillator 8, a self-oscillation type or master oscillation power-amplifying type can be used. The master oscillation power-amplifying type is more favorable than the self-oscillation type. More specifically, as shown in FIG. 12, the ultrasonic oscillator 8 has a high frequency oscillation part 33 having a high frequency ultrasonic wave oscillator 31 and a power amplifier 32, and an output adjuster 34. The ultrasonic vibrator 4 (5) is electrically connected to the high frequency oscillation part 33 via the output adjuster 34. The oscillation frequency of the high frequency ultrasonic wave oscillator 31 is equal to the resonance frequency of the ultrasonic vibrator. In the range in which a necessary high-frequency electric power is generated in a load-applied state when an ultrasonic energy emitted by the ultrasonic vibrator is used, the voltage to be applied to the ultrasonic vibrator may be increased, and the oscillation frequency of the high frequency ultrasonic wave oscillator 31 may be set a little higher than the resonance frequency of the ultrasonic vibrator. This is because the resonance frequency of the ultrasonic vibrator at the time when a load is applied thereto is a little higher than that of the ultrasonic vibrator when no load is applied thereto. As shown in FIG. 13, a high frequency oscillation part 33 and an output adjuster 34 may be provided for each of the ultrasonic vibrators 4, 5.

The ultrasonic oscillator 8 has the connector connection portion 9 connected to the connector 3 of the cleaning catheter 2.

The lead wire 6 of each vibrator is connected to the terminal 7 of the connector 3. By connecting the connector 3 to the connector connection portion 9 of the ultrasonic oscillator 8, the vibrators 4, 5 are electrically connected to the output adjuster 34 of the ultrasonic wave oscillator 8.

The ultrasonic oscillator 8 may function to adjust the ultrasonic wave generation state. It is possible to provide the ultrasonic oscillator 8 with a function to alter the sound output of the ultrasonic wave of the ultrasonic vibrator and an operation-adjusting function to change the operation of the ultrasonic vibrator successively or intermittently.

The cleaning apparatus 1 for cleaning the inside of the channel of the medical instrument of the embodiment includes the cleaning liquid discharge device 13 having the cleaning liquid-feeding tube 10 into which the cleaning catheter 2 can be inserted with the ultrasonic vibrator exposed and which jets the cleaning liquid from the front end thereof, the cleaning liquid-storing tank 14, and the liquid-feeding pump 16 for feeding the cleaning liquid.

The front end of the cleaning liquid-feeding tube 10 is open and its rear end is fitted into an L-shaped fixing supporting pipe 20. The length of the cleaning liquid-feeding tube 10 is favorably in the range of 50–200 cm and more favorably in the range of 150–180 cm. The outer diameter of the cleaning liquid-feeding tube 10 is favorably in the range of 1.5–5.5 mm and more favorably in the range of 2.2–2.8 mm. The inner diameter of the cleaning liquid-feeding tube 10 is favorably in the range of 1.4–5.4 mm and more favorably in the range of 2.1–2.7 mm.

As the material for the cleaning liquid-feeding tube 10, the following thermoplastic resins are preferable: olefin resins such as polyethylene, polypropylene, polybutylene, ethylene-vinyl acetate copolymer or polyolefin elastomers thereof, fluorocarbon resin or soft fluorocarbon resin, methacrylate resin, polyphenylene oxide, modified polyphenylene ether, polyethylene terephthalate, polybutylene terephthalate, polyurethane elastomer, polyester elastomer, polyamide or polyamide elastomer, polycarbonate, polyacetal, styrene resin or styrene elastomer, and thermoplastic polyimide. It is possible to use a polymer alloy or a polymer blend containing any one or more of these resins as a base material thereof.

An unshown rigidity-imparting member may be mounted on the cleaning liquid-feeding tube 10 to prevent bending of the body thereof and suppress expansion thereof. It is preferable to arrange the rigidity-imparting member in the range from the rear end of the cleaning liquid-feeding tube 10 to the vicinity of the front end thereof.

It is preferable that the rigidity-imparting member is reticulate. It is preferable that the reticulate rigidity-imparting member is made of braided wires. The rigidity-imparting member can be formed of metal wires of stainless steel, elastic metal, ultra-high elastic alloy, or shape-storing alloy. The diameter of the metal wire is favorably in the range of 0.01–0.2 mm and more favorably in the range of 0.03–0.1 mm. The rigidity-imparting member may be formed of synthetic fibers such as polyamide fiber, polyester fiber, and polypropylene fiber.

As shown in FIG. 5, the cleaning liquid-feeding tube 10 has a plurality of ribs 11 extending from the inner peripheral surface thereof toward its center so as to allow the interval between the cleaning liquid-feeding tube 10 and the cleaning catheter 2 to be almost uniform around the entire circumference thereof. It is preferable that the rib 11 is formed in the axial direction of the cleaning liquid-feeding tube 10 over the entire length thereof. In the embodiment shown in FIG. 5, a plurality of the ribs 11, namely, the partitioning walls 11 are formed longitudinally and parallel with one another on the inner surface of the cleaning liquid-feeding tube. The ribs 11 may be dotted on the inner surface of the cleaning liquid-feeding tube. In this case, it is preferable to arrange the ribs 11 in the axial direction of the cleaning liquid-feeding tube 10.

The rib 11 allows the cleaning catheter 2 and the cleaning liquid-feeding tube 10 to be almost coaxial with each other and the interval between the cleaning liquid-feeding tube 10 and the cleaning catheter 2 to be almost uniform around the entire circumference thereof. Accordingly, the diluted solution containing cleaning chemicals is jetted almost uniformly around the peripheral surface of the front side of the cleaning catheter. Thus the inner surface of the channel of the medical instrument can be washed reliably and uniformly.

At the front end of the L-shaped fixing supporting pipe 20 there is formed a mounting opening into which the cleaning liquid-feeding tube 10 is fitted. At a position facing the mounting opening of the L-shaped fixing supporting pipe 20 there is formed an insertion opening into which the cleaning catheter is inserted. The insertion opening is provided with an unshown O-ring to make the gap between the inserted cleaning catheter and the insertion opening liquid-tight. A male portion 19a of a tube connection connector is formed at the rear end of the L-shaped fixing supporting pipe 20.

The cleaning catheter 2 is inserted into the cleaning liquid-feeding tube 10 in such a way that the front side of the cleaning catheter 2 on which the ultrasonic vibrators 4, 5 have been mounted is projected beyond the front end of the cleaning liquid-feeding tube 10. Thereafter, the cleaning catheter 2 is fixed.

The cleaning liquid discharge device 13 has the tank 14 storing the cleaning liquid, a cleaning liquid-sucking nozzle 15 inserted into the tank 14, and a liquid-feeding pump 16 connected to the upper portion of the cleaning liquid-sucking nozzle 15. The cleaning liquid discharge device 13 also has a liquid pressure-adjusting knob 17 that adjusts the pressure of the cleaning liquid drawn from the pump 16. One end of a feeding tube 18 is connected to the liquid-feeding pump 16 at its feeding side. A female portion 19b of the tube connection connector is installed at the other end of the feeding tube 18. The feeding tube 18 and the cleaning liquid-feeding tube 10 communicate with each other by connecting the male portion 19a of the tube connection connector of the cleaning liquid-feeding tube 10 and the female portion 19b of the tube connection connector to each other. The cleaning liquid supplied at a high pressure from the cleaning liquid discharge device 13 is jetted strongly forward from the gap between the cleaning catheter 2 and the cleaning liquid-feeding tube 10 through the feeding tube 18 and the cleaning liquid-feeding tube 10.

The method of the present invention for cleaning the inside of the channel of the medical instrument will be described below.

The method of the present invention for cleaning the inside of the channel of the medical instrument has the step of inserting the cleaning catheter 2 having the ultrasonic vibrators 4, 5 mounted thereon and the cleaning liquid-feeding tube 10, for expelling the cleaning liquid, provided in such a way as to surround the cleaning catheter 2 with the ultrasonic vibrator exposed into the channel 12 of the medical instrument and the step of expelling the cleaning liquid from the gap between the cleaning catheter 2 and the cleaning liquid-feeding tube 10 and operating the ultrasonic vibrators 4, 5 to separate a matter from the matter-adhered inner surface of the channel 12 of the medical instrument by the ultrasonic vibration and carry the separated matter forward by means of the jetted cleaning liquid.

It is preferable to use the cleaning liquid as a medium for transmitting the vibration of the ultrasonic vibrator to the inner surface of the channel.

Description is made on the step of inserting the cleaning catheter 2 having the ultrasonic vibrators 4, 5 mounted thereon and the cleaning liquid-feeding tube 10, for expelling the cleaning liquid, provided in such a way as to surround the cleaning catheter 2 with the ultrasonic vibrator exposed into the channel 12 of the medical instrument Initially, a predetermined amount of the cleaning liquid is injected into the tank 14. As the cleaning liquid, it is possible to use a diluted solution containing cleaning chemicals (for example, liquid containing lipid-decomposing enzyme and liquid containing protein-decomposing enzyme), sterile water, distilled water, RO water, ethyl alcohol-containing water, and physiologic saline.

It is possible to perform a pre-treatment step consisting of filling the diluted solution containing cleaning chemicals, for example, the liquid containing the lipid-decomposing enzyme and the liquid containing the protein-decomposing enzyme into the channel of the medical instrument and allowing the diluted solution containing cleaning chemicals to stand for a predetermined period of time before inserting the cleaning liquid-feeding tube 10 into which the cleaning catheter 2 has been fixedly inserted into the channel 12. The pre-treatment process can be performed by immersing the to-be-cleaned medical instrument in a bath into which the diluted solution containing cleaning chemicals has been injected. The cleaning method of the present invention can be reliably achieved by carrying out the pretreatment process.

Thereafter, the cleaning liquid-feeding tube 10 into which the cleaning catheter 2 has been fixedly inserted (hereinafter referred to as cleaning catheter-installed cleaning liquid-feeding tube) with the ultrasonic vibrator exposed is inserted into an end of the to-be-cleaned channel (for example, clamp channel, suction channel, liquid-feeding tube, air-feeding tube). The cleaning method of the present invention will be described below by exemplifying the case in which the inner surface of the suction channel is cleaned.

Description is made on the step of expelling the cleaning liquid from the gap between the cleaning catheter 2 and the cleaning liquid-feeding tube 10 and operating the ultrasonic vibrators 4, 5 to separate the matter from the matter-adhered inner surface of the channel 12 of the medical instrument by an ultrasonic vibration and carry the separated matter forward by means of the jetted cleaning liquid.

More specifically, the liquid-feeding pump 16 is actuated to allow the suction nozzle 15 to suck up the cleaning liquid. Then, the pressurized cleaning liquid is fed to the supply tube 18 to supply the cleaning liquid under high pressure to the cleaning liquid-feeding tube 10 via the male and female portions 19*a* and 19*b* of the tube connection connector and the L-shaped fixing supporting pipe 20. Further, the ultrasonic oscillator 8 is actuated to emit the ultrasonic wave from the ultrasonic vibrators 4, 5.

The ultrasonic wave emitted from the ultrasonic vibrators 4, 5 is transmitted to the inner surface of the suction channel through the cleaning liquid jetted from the gap between the front end of the cleaning liquid-feeding tube 10 and the confronting portion of the cleaning catheter 2 serving as the transmission medium. The ultrasonic vibration pulverizes matter that has adhered to the inner surface of the suction channel. As a result, the contaminant separates gradually from the inner surface of the suction channel and floats up therefrom. The cleaning liquid jetted from the cleaning liquid-feeding tube 10 flows forward with the cleaning liquid enclosing the contaminant. The stream of cleaning liquid forcibly washes the inner surface of the suction channel, thereby discharging bacteria, viruses, secretion, and blood. In his manner, the inner surface of the suction channel is cleaned.

It can be said that when the ultrasonic wave is imparted to the cleaning liquid, cavitation occurs and thereby the matter that has adhered to the inner surface of the suction channel separates therefrom. In other words, it is desirable to emit the ultrasonic wave from the ultrasonic vibrator and supply the cleaning liquid to the cleaning liquid-feeding tube 10 in such a way as to generate cavitation in the vicinity of the inner surface of the channel of the medical instrument.

After the cleaning catheter-installed cleaning liquid-feeding tube is inserted into the other end of the channel of the medical instrument, it is reciprocated axially and twisted. This permits the ultrasonic vibration to be imparted to the entire inner surface of the suction channel.

The present invention is not limited to the embodiments that have been described above. Different embodiments of the present invention may be made without departing from the spirit and scope thereof.

For example, the cleaning apparatus is applicable to the cleaning of the inner surface of the channel of laproscopes and breathing circuits used in examination and treatment, contaminated examination/treatment tools used on patients, operation tools used in surgical operation, instruments used in bacterium examination, contaminated instruments used in biological experiments, and mechanical instruments contaminated with bacteria or viruses.

The cleaning apparatus of the present invention for cleaning the inside of the channel of the medical instrument is embodied in the above-described mode and has effects described below.

According to the method and apparatus of the present invention for cleaning the inside of the channel of the medical instrument, it is possible to insert the cleaning catheter on which the ultrasonic vibrator has been installed into the channel of the medical instrument and move the cleaning catheter in the channel while the ultrasonic wave is being emitted from the ultrasonic vibrator. Thus, it is possible to repeatedly apply the ultrasonic vibration to the contaminated inner surface of the channel of the medical instrument from a position close to the inner surface of the channel. Therefore, it is possible to separate a contaminant from the inner surface of the channel to which it has adhered.

According to one embodiment of the apparatus, the ultrasonic vibrator is provided at the front end of the cleaning catheter. Therefore, it is possible to impart the ultrasonic vibration to the contaminated inner surface of the channel forward in a wide range from the cleaning catheter in a cleaning catheter insertion direction.

According to one embodiment of the apparatus, the ultrasonic vibrator is provided on the peripheral surface of the cleaning catheter. Thus, the ultrasonic vibration acts on the contaminated inner surface of the channel from a position close to the inner surface of the channel and almost perpendicularly to the contaminated inner surface of the channel. Therefore, it is possible to reliably separate a matter from cavities or flaws present on the matter-adhered inner surface of the channel.

According to another embodiment of the apparatus, ultrasonic vibrators are installed at the front end of the cleaning catheter and on the peripheral surface of the cleaning catheter. Thus, it is possible to repeatedly impart the ultrasonic vibration in many directions towards the contaminated inner surface of the channel. Therefore, it is possible to securely separate a matter from the matter-adhered inner surface of the channel of the medical instrument.

According to one aspect of the method of the invention, in addition to the ultrasonic vibration, the cleaning liquid can be jetted or expelled inside the narrow channel. Therefore, it is possible to effectively separate undesirable matter from the inner surface of the channel.

In another embodiment of the apparatus, the interval between the cleaning liquid feeding tube and the cleaning catheter is almost uniform around the entire circumference of the cleaning liquid feeding tube and the cleaning catheter. Therefore, the cleaning liquid can be expelled radially and uniformly from the gap and is capable of washing the entire inner surface of the channel.

What is claimed is:

1. A cleaning apparatus for cleaning an inside of a channel of a medical instrument, said cleaning apparatus comprising:

a cleaning catheter having a plurality of ultrasonic vibrators, of which a first ultrasonic vibrator is provided at a front end of said cleaning catheter and a second ultrasonic vibrator is provided on a peripheral surface of said cleaning catheter; and an ultrasonic oscillator provided at a front end of said cleaning catheter and comprising a vibration direction conversion member that converts a longitudinal vibration into a radial vibration, said ultrasonic oscillator operates said ultrasonic vibrator.

2. A cleaning apparatus for cleaning an inside of a channel of a medical instrument, said cleaning apparatus comprising:

an ultrasonic wave cleaning device comprising a cleaning catheter provided with an ultrasonic vibrator for separating a matter from a matter-adhered inner surface of said channel of said medical instrument by an ultrasonic vibration;

an ultrasonic oscillator for operating said ultrasonic vibrator; and a cleaning liquid discharge device comprising a cleaning liquid-feeding tube into which said cleaning catheter can be inserted with said ultrasonic vibrator exposed and which jets a cleaning liquid from a front end thereof, a cleaning liquid-storing tank and a pump for feeding said cleaning liquid.

3. A cleaning apparatus according to claim 2, wherein said cleaning liquid-feeding tube has a plurality of ribs extending from an inner surface thereof toward a center thereof to allow an interval between said cleaning liquid-feeding tube and said cleaning catheter to be almost uniform in an entire circumference of said cleaning liquid-feeding tube and said cleaning catheter.

4. A cleaning apparatus according to claim 2, wherein said ultrasonic vibrator is provided at a front end of said cleaning catheter.

5. A cleaning apparatus according to claim 4, wherein said ultrasonic vibrator provided at a front end of said cleaning catheter comprises a vibration direction conversion member that converts a longitudinal vibration into a radial vibration.

6. A cleaning apparatus according to claim 2, wherein said ultrasonic vibrator is provided on a peripheral surface of said cleaning catheter.

7. A cleaning apparatus according to claim 2, wherein said cleaning catheter has a plurality of ultrasonic vibrators, of which a first ultrasonic vibrator is provided at a front end of said cleaning catheter and a second ultrasonic vibrator is provided on a peripheral surface of said cleaning catheter.

* * * * *